US005499631A

United States Patent [19]
Weiland

[11] Patent Number: 5,499,631
[45] Date of Patent: Mar. 19, 1996

[54] METHOD OF MEASURING THE ELECTRIC CONDUCTIVITY OF BODY FLUIDS, AND TEST PROBE FOR CARRYING OUT THE METHOD

[75] Inventor: Werner Weiland, Bendorf-Sayn, Germany

[73] Assignee: Rheintechnik Weiland & Kaspar KG Maschinenfabrik, Benford, Germany

[21] Appl. No.: 244,035

[22] PCT Filed: Nov. 10, 1992

[86] PCT No.: PCT/EP92/02573

§ 371 Date: May 12, 1994

§ 102(e) Date: May 12, 1994

[87] PCT Pub. No.: WO93/09716

PCT Pub. Date: May 27, 1993

[30] Foreign Application Priority Data

Nov. 13, 1991 [DE] Germany .................. 41 37 303.0

[51] Int. Cl.⁶ ................................................ A61B 10/00
[52] U.S. Cl. ................................................ 128/734
[58] Field of Search ......................... 128/734, 738, 128/778; 607/138

[56] References Cited

U.S. PATENT DOCUMENTS

| | | | |
|---|---|---|---|
| 3,844,276 | 10/1974 | McDougall | 128/734 |
| 4,224,949 | 9/1990 | Scott et al. | 128/734 |
| 4,498,481 | 2/1985 | Lemke | 128/734 |
| 4,685,471 | 8/1987 | Regas et al. | 128/734 |

Primary Examiner—Max Hindenburg
Attorney, Agent, or Firm—Max Fogiel

[57] ABSTRACT

A method of measuring the electric conductivity of body fluids. It uses several test electrodes positioned at various sites at one area of the body to determine electric resistance. The measurements are obtained with a test probe that accommodates the test electrodes. The resistances detected by the test electrodes are polled and the minimal resistance is exploited as a reference for determining electric conductivity. The test probe employed to carry out the method is characterized by a large number of point-shaped test electrodes distributed over the surface of the test probe and associated with the same grounding device.

19 Claims, 2 Drawing Sheets

METHOD OF MEASURING THE ELECTRIC CONDUCTIVITY OF BODY FLUIDS, AND TEST PROBE FOR CARRYING OUT THE METHOD

BACKGROUND OF THE INVENTION

The search for satisfactory methods of detecting estrus in farm animals has long been a subject of scientific interest. The same is true with respect to detecting the exact moment of ovulation in women.

SUMMARY OF THE INVENTION

To establish the optimal moment for insemination in farm animals research has been undertaken to discover ways of exploiting hormone analysis, changes in the electric conductivity of the vaginal mucous membrane, vaginal pH, vaginal cytology, and body temperature. Up to now, however, there are hardly any practical methods.

European Patent 0 177 994 describes a method of predicting ovulation in women. The beginning of menstruation is recorded and a body parameter that regularly supplies information about the menstrual cycle established. This parameter is the specific electric resistance of the subject's saliva. The document also proposes determining the electric resistance of the vaginal mucus at the beginning of determination of the first peak in the chart of the salivary resistance, whereby the vaginal electric resistance is maintained daily. The increase in vaginal resistance subsequent to a minimum simultaneously indicates to the user the presence of ovulation. The publication describes in this context a test probe for determining the electric resistance of the saliva. The test probe has a flat surface with several circular test electrodes embedded in it. The same publication describes a cylindrical test probe surrounded by annular test electrodes and with rounded ends for determining the electric resistance of the vaginal mucus. The test electrodes in both test probes measure parallel.

One object of the present invention is an exact method of measuring the electric conductivity of body fluids. The second is a test probe that can be practically employed in conjunction with the method.

The method of measuring the electric conductivity of body fluids in accordance with the invention uses several test electrodes positioned at various sites at one area of the body to determine electric resistance. The measurements are obtained with a test probe that accommodates the test electrodes. The method is characterized in that the resistances detected by the test electrodes are polled and the minimal resistance is exploited as a reference for determining electric conductivity.

The invention takes into account that the test probe and hence the test electrodes constantly change position relative to the adjacent body wall due to the motion of the human or other animal during the measurement of the electric conductivity of body fluids, especially during the measurement of the electric conductivity of vaginal or cervical mucus. The test electrodes will accordingly more or less contact the body fluid. The desired signal is accordingly powerfully affected by the volume and spatial distribution of the mucus. It depends, in other words, on the position of the testing site. The method in accordance with the invention counteracts this dependency first by measuring at several different sites within the area. Changes in signal due to changes in the electric conductivity of the mucus must accordingly appear as tendencies at each site. The various sites are obtained by positioning a large number of test electrodes. Since each test electrode is separately circuited it is possible in order to determine the resistance to evaluate only the test electrode that has the lowest resistance.

Evaluation of the lowest resistance provides information as to whether the particular test electrode is taken into consideration that is most washed with mucus and accordingly lies in the freshest mucus. In terms of determining ovulation it is known that the electric resistance of the cervical and/or vaginal mucus is highest prior to ovulation and decreases as ovulation approaches while the volume of mucus simultaneously increases when necessary. The low resistance due to optimal positioning of the single test electrode being exploited for evaluation and the tendency toward decreased resistance at the approach of ovulation correlate therewith. Thus, due to the method in accordance with the invention one attains high independence of mucous volume and position of test probe or test electrodes, whereby one can assume that the test electrode with the lowest resistances is completely soaked in body fluid. This value is exploited to construct an algorithm.

In practical terms there occurs with the test electrodes a point-by-point measurement, meaning that point-shaped test electrodes are employed. Measurement of conductivity occurs in practical terms in the form of long-term measurement at defined intervals. There accordingly occurs a continuous detection of the conductivity of the body fluid. The electric resistances are stored and can be subsequently processed. Measurement of the test electrodes with subsequent detection of the lowest resistance can for example be carried out at intervals as brief as a quarter, half, or whole minute.

Since body fluids are as a general rule electrolytes, which is especially true of mucus, measurement must be carried out with alternating current to prevent polarization. The detected resistance will accordingly not present itself as strictly ohmic but in the form of impedance. The method should be designed to ensure that the result will be an absolute impedance magnitude.

It is considered particularly advantageous when in addition to detecting the electric conductivity of the body fluid, ion releases in the body fluid and/or body temperature are detected. The detection of these references should occur in particular during the determination of ovulation.

The test probe preferably employed to carry out the method features a large number of point-shaped test electrodes distributed over the surface of the test probe and associated with the same grounding device. When one considers that the current flowing between one pair of conductors, specifically the point-shaped test electrode and its associated frame, is not restricted to the shortest path but distributes itself over all available paths, the result is two advantageous embodiments of the test probe. The first exhibits concentric with the particular point-shaped test electrode a conductive grounding ring, whereby a ring of insulation is positioned between the pair of conductors comprising the point-shaped test electrode and its associated grounding ring. The second has a ring of insulation around each point-shaped test electrode and the remaining surface of the test probe has a conductive grounding surface. The probe support for the point-shaped test electrodes and the grounding rings or conductive grounding surface are naturally made of insulating material. To prevent signal changes due to oxidation processes the point-shaped test electrodes and the grounding rings or grounding surface are made of a non-oxidizing conductive material, gold for example.

If the test probe is inserted into the vagina, it is for practical purposes cylindrical with rounded ends or in the form of a ball. It can also exhibit ion-sensitive test electrodes and/or temperature test electrodes embedded in its surface. The evaluation units can be accommodated inside the test probe so that they can be read into a memory subsequent to removal of the test probe from the body. It is on the other hand also possible to establish an electric connection between the test probe and the evaluation units positioned outside the body.

DESCRIPTION OF THE PREFERRED EMBODIMENTS

Figure 1:
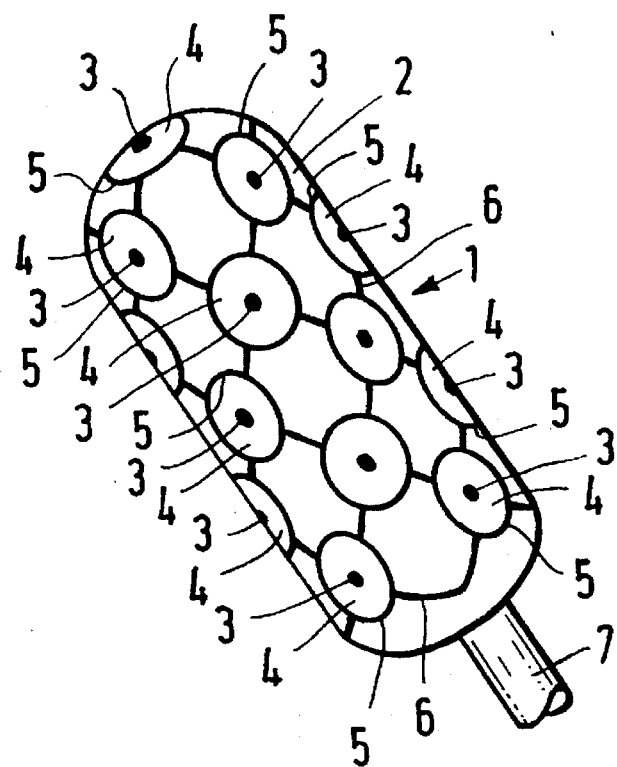
FIGS. 1 through 3 represent details with reference to two possible embodiments of the test probe in accordance with the invention and of the method in accordance with the invention.

FIG. 1 is a top view of a cylindrical test probe 1 with rounded ends. Regularly position, at the same distance from one another, that is, over the probe surface 2 are a number of point-shaped test electrodes 3. Each point-shaped test electrode 3 is surrounded by a ring 4 of insulation that is itself surrounded by a grounding ring 5 concentric with point-shaped test electrode 3. Point-shaped test electrodes 3 and grounding rings 5 are gold. Grounding rings 5 are connected by lines 6. Point-shaped test electrodes 3 are connected separately. The connection between test probe 1 and external assemblies not illustrated more specifically in this figure is represented by a connecting cable 7.

Figure 2:
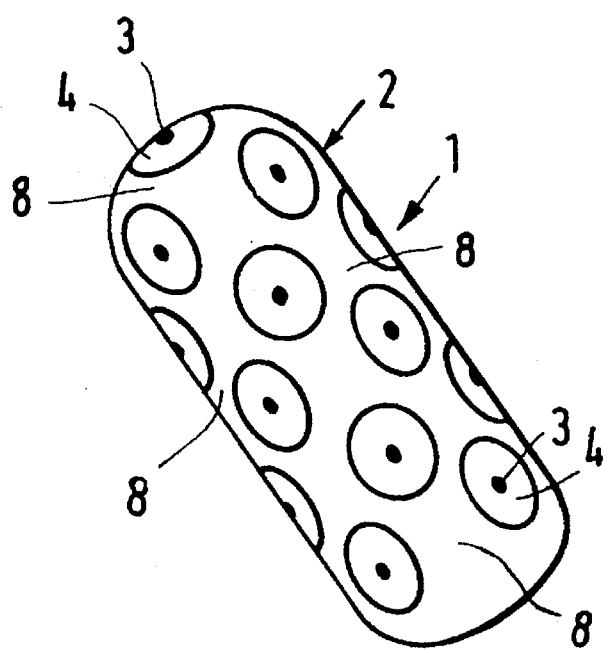

The test probe 1 illustrated in FIG. 2 is essentially similar to the one illustrated in FIG. 1. It has point-shaped test electrodes 3 surrounded by rings 4 of insulation on its probe surface 2. Instead of grounding ring 5, the rest 8 of the test-probe surface between rings 4 of insulation exhibits a conductive grounding surface. This and the point-shaped electrodes consist of gold. In contrast to the embodiment illustrated in FIG. 1, a processing-and-memory unit for the detected measurement values is accommodated in test probe 1. The values are represented subsequent to removal of test probe 1 from the body opening.

Figure 3:
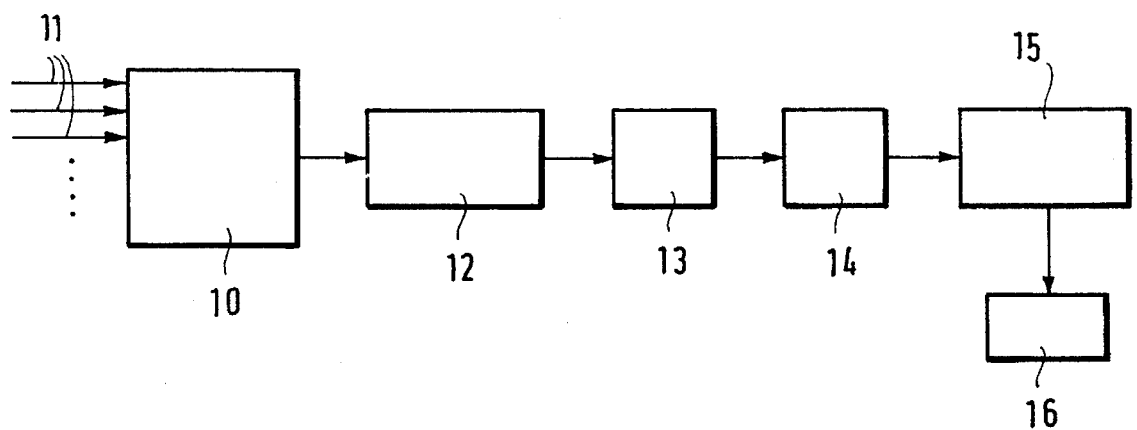

FIG. 3 is a block diagram for estrus detection, for detecting estrus in cows for example. Impedance channels 11 corresponding to the number of point-shaped test electrodes 3, sixteen impedance channels for example, are transmitted to an alternate-to-direct current converter 12 through a multiplexer 10. From the sixteen values, which are initially deposited in an intermediate buffer 13, an arithmetic unit (ALU) 14 determines the value with the lowest impedance. This selected impedance value is deposited in an internal memory 15. A serial interface stores either a short high-frequency transmission section or an inductive transmission 16. External reading equipment intercepts the content of the memory every day and processes the data for estrus detection. Characteristic of estrus is a definite drop in the impedance curve from approximately 60 ohms to approximately 10 to 20 ohms, which basically follows the animal's temperature curve. A current-saving circuit should be provided to ensure the reliability of the circuit for thirty-five days.

The overall circuit comprises several components:
Sensor
    Mixed analog-digital ASIC: Amplifier, multiplexer, ac-dc converter, ALU unit (logic gate), RAM
    Discrete technology: Inductive transmission or high-frequency transmitter
    Reading equipment consisting of: Receiving section (inductive or high-frequency), µ processor, long-term memory, input-output units Sensor, ASIC, and telemetry section should be constructed miniaturized so that introduction into the cow's vagina is possible. In this application the complete size of the sensor should be matched to the particular vaginal configuration.

A corresponding design of the test probe with smaller dimensions is employed to detect ovulation in women, and furthermore an appropriate processing circuit. The test probe consists on the whole of physiologically unobjectionable material.

I claim:

1. A method for measuring electrical conductivity of body fluids comprising the steps of: positioning a plurality of test electrodes at various sites on one area of a body to determine electrical resistance; taking measurements with said test electrodes; detecting resistances by said test electrodes; evaluating said resistances detected by said test electrodes and obtaining a minimal resistance; designating the minimal resistance as a reference for determining electrical conductivity; and providing a common ground for said test electrodes, whereby the electrical conductivity of body fluids is measured through said test electrodes.

2. A method as defined in claim 1, wherein a point-by-point measurement is taken with the test electrodes.

3. A method as defined in claim 1, wherein a measurement of conductivity is taken in form of long-term measurements at specific intervals.

4. A method as defined in claim 1, wherein said intervals are a quarter, half, or whole minute.

5. A method as defined in claim 1, wherein the body fluid is cervical and/or vaginal mucus of human and/or other animal, said measurements occurring said test electrodes in a cervix or vagina for detecting estrus or determining ovulation.

6. A method as defined in claim 1, wherein a measurement is carried out with alternating current and the resistance comprises impedance.

7. A method as defined in claim 1, wherein said measurement is in form of an absolute impedance magnitude.

8. A method as defined in claim 1, including the step of detecting ion releases in the body fluids and/or body temperatures in addition to detecting electrical conductivity of the body fluids.

9. An arrangement for measuring electrical conductivity of body fluids, comprising a plurality of test electrodes positioned at various sites on one area of a body to determine electrical resistance; means for taking measurements with the test electrodes; means for detecting electrical resistances by said test electrodes; means for evaluating said resistances detected by said test electrodes and obtaining a minimal resistance, said minimal resistance being designated as a reference for determining electrical conductivity; common grounding means, said test electrodes being point-shaped and distributed over a surface of said arrangement and associated with said common grounding means, whereby the electrical conductivity of body fluids is measured through said test electrodes.

10. An arrangement as defined in claim 9, wherein said grounding means comprises a conductive grounding ring concentric to a respective point-shaped test electrode; a ring of insulation positioned between a pair of conductors comprising said respective point-shaped test electrode and said grounding ring.

11. An arrangement as defined in claim 10, wherein the point-shaped test electrodes and respective grounding rings are made of a non-oxidizing conductive material.

12. An arrangement as defined in claim 11, wherein said non-oxidizing conductive material is gold.

13. An arrangement as defined in claim 9, including a ring of insulation around each point-shaped test electrode, said test probe having a remaining surface with a conductive grounding surface.

14. An arrangement as defined in claim 9, wherein said test probe is cylindrical with rounded ends.

15. An arrangement as defined in claim 9, wherein said test electrodes are ion-sensitive.

16. An arrangement as defined in claim 9, wherein said test probe is cylindrical with ball-shaped ends.

17. An arrangement as defined in claim 9, wherein said test electrodes are temperature sensing electrodes.

18. An arrangement as defined in claim 9, wherein said test electrodes are ion-sensitive and temperature sensitive.

19. An arrangement for measuring electrical conductivity of body fluids, comprising a plurality of test electrodes positioned at various sites on one area of a body to determine electrical resistance; means for taking measurements with the test electrodes; means for detecting electrical resistances by said test electrodes; means for evaluating said resistances detected by said test electrodes and obtaining a minimal resistance, said minimal resistance being designated as a reference for determining electrical conductivity; common grounding means, said test electrodes being point-shaped and distributed over a surface of said arrangement and associated with said common grounding means; said grounding means comprising a conductive grounding ring concentric to a respective point-shaped electrode; a ring of insulation positioned between a pair of conductors comprising said respective pointshaped test electrode and said grounding ring; a ring of insulation around each point-shaped test electrode, said test electrodes having a remaining surface with a conductive grounding surface; said point-shaped test electrode and respective grounding rings being made of a non-oxidizing conductive material; said test electrodes being cylindrical with rounded ends; said test electrodes being ion-sensitive and temperature-sensitive, whereby the electrical conductivity of body fluids is measured through said test electrodes.

\* \* \* \* \*